(12) United States Patent
Yoshida et al.

(10) Patent No.: US 6,235,911 B1
(45) Date of Patent: May 22, 2001

(54) 5-AMINOPYRAZOLE-4-CARBOXYLATE DERIVATIVE AND PROCESS FOR PREPARING THE SAME

(75) Inventors: Kei Yoshida; Shingo Matsuo; Toshio Kitashima; Kanji Tomiya; Kenji Kodaka, all of Chiba-ken (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/580,117

(22) Filed: May 30, 2000

(30) Foreign Application Priority Data

Jun. 18, 1999 (JP) .................................. 11-172031

(51) Int. Cl.$^7$ ................................ C07D 231/38
(52) U.S. Cl. ............................................. 548/372.5
(58) Field of Search .......................... 548/372.5

(56) References Cited

U.S. PATENT DOCUMENTS 5,608,077 * 3/1997 Hattou et al. ..................... 548/372.5

OTHER PUBLICATIONS

Hatton et al, *Chemical Abstracts*, vol. 07 No. 213615, 1987.*
Hatton et al, *Chemical Abstracts*, vol. 120 No. 248625, 1994.*

* cited by examiner

Primary Examiner—Robert W. Ramsuer
(74) Attorney, Agent, or Firm—Burns, Doane, Swecker, & Mathis, L.L.P.

(57) ABSTRACT

A 5-aminopyrazole-4-carboxylate derivative represented by the formula (1) is prepared by reacting a compound represented by the formula (2) with a hydrazine compound represented by the formula (3) or hydrate, hydrochloride, hydrobromide or sulfate of the same according to the reaction formula (C):

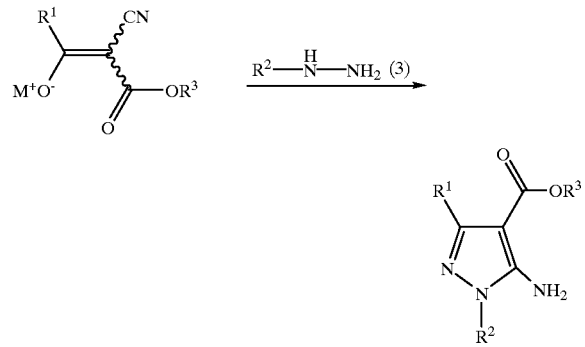

wherein $R^1$ is a straight or branched C1 to C4 alkyl group which can be substituted with a halogen atom, $R^2$ is a hydrogen atom, straight or branched C1 to C4 alkyl group or an unsubstituted or substituted phenyl group, and $R^3$ is a straight or branched C1 to C4 alkyl group, and M is an alkali metal.

The 5-aminopyrazole-4-carboxylate derivative obtained by the preparation process of the invention is useful for an intermediate of agricultural chemicals and medicines, fungicides in particular.

19 Claims, No Drawings

5-AMINOPYRAZOLE-4-CARBOXYLATE DERIVATIVE AND PROCESS FOR PREPARING THE SAME

BACKGROUND OF THE INVENTION

1. Field of the Invention

The present invention relates to a 5-aminopyrazole-4-carboxylate derivative which is an important intermediate of medicines and agricultural chemicals, and process for preparing the same. For example, ethyl 5-amino-1-methyl-3-trifluoromethylpyrazole-4-carboxylate can be prepared by the process of the invention and can be converted to a useful intermediate for agricultural chemicals, ethyl 1-methyl-3-trifluoromethylpyrazole-4-carboxylate (Japanese Laid-Open Patent Hei 1-106866), by diazotization and successive elimination of amino group according to a known technique.

2. Prior Art

Various compounds having a pyrazole skeleton have been known as medicines, agricultural chemicals and fungicides in particular. Accordingly, it has been strongly desired to develop a process for efficiently preparing the compounds having the pyrazole skeleton. Particularly, 5-aminopyrazole-4-carboxylate derivatives are important intermediates for preparation in the field.

Conventionally, various preparation processes have been known for the 5-aminopyrazole derivatives. For example, Japanese Patent Gazette Hei 6-503069 has described a process for preparing various 5-aminopyrazole derivatives by condensation of a cyanoalkenyl compound represented by the formula (5):

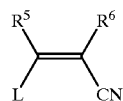

(5)

wherein L is a C1 to C4 alkoxy group, $R^5$ is a hydrogen atom or an unsubstituted or halogen substituted C1 to C4 alkyl group, and $R^6$ is cyano group, —CO—$R^7$ group or —CS—$R^7$ group, wherein $R^7$ is a hydroxy group, C1 to C4 alkoxy group, amino group, C1 to C4 alkylamino group or di (C1 to C4)alkylamino group, in the presence of a base with a hydrazine compound represented by the formula (6):

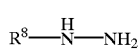

(6)

wherein $R^8$ is a phenyl group which can be substituted with a C1 to C8 alkyl group or C1 to C8 hydroxyalkyl group having no substitution or further substitution with 1 to 3 halogen atoms, nitro group, C1 to C4 alkyl group, partially or wholly halogenated C1 to C4 alkoxy group, C1 to C4 alkylthio group or —$NR^9R^{10}$ groups, wherein $R^9$ and $R^{10}$ are hydrogen atoms or C1 to C4 alkyl groups, and the phenyl group can additionally have totally 4 or 5 halogen atoms.

*J. Heterocycl. Chem.* 12 1199–1205 (1975) has reported a process for preparing a 4-cyano-5-aminopyrazole derivative according to the following reaction formula (A):

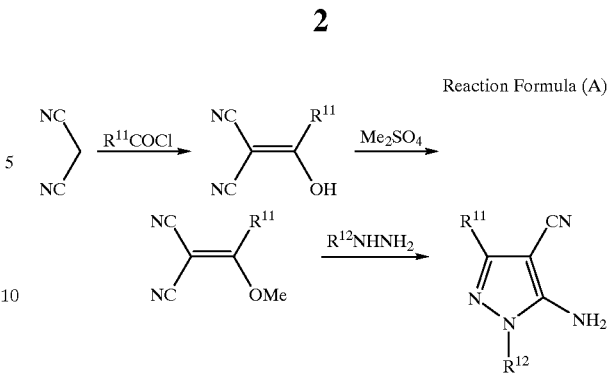

Reaction Formula (A)

wherein $R^{11}$ is a phenyl group, p-substituted phenyl group or p-substituted benzyl group and $R^{12}$ is a hydrogen atom, a methyl group or hydroxyethyl group.

In these processes, the cyanoalkene derivative used for condensation with the hydrazine derivative is a β-alkoxyacrylonitrile derivative.

The example of a substituent other than an alkoxy group on the portion L (eliminating group) in the formula (5) has been described in *Zh. Org. Khim.* 17, No. 2, 268–272 (1981). In the report, 5-aminopyrazole-4-carboxylate has been prepared according to the reaction formula (B):

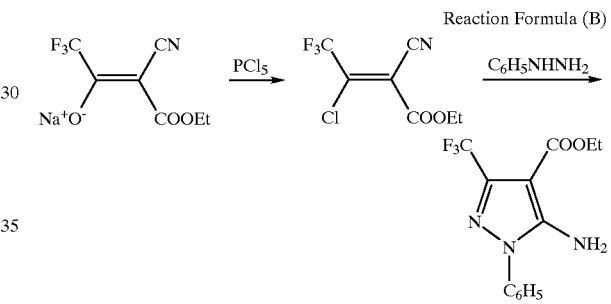

Reaction Formula (B)

5-Aminopyrazole-4-carboxylate derivative is prepared by chlorinating an alkali metal salt of 3-hydroxy-2-ene-carboxylate with phosphorous pentachloride and successively reacting the resultant 2-chlorocyanoalkene derivative with a hydrazine derivative. In the process, isomers of the aminopyrazole derivative tend to form.

As mentioned above, the known process for preparing the 5-aminopyrazole-4-carboxylate derivative uses an alkoxy group or chlorine atom for the eliminating group, and thus excessive steps are required for preparing the raw material cyanoalkene derivative.

Consequently, the object of the present invention is to provide a novel preparation process of 5-aminopyrazole-4-carboxylate derivative which can be efficiently carried out with ease in industry and has a low tendency to form isomers and a novel 5-aminopyrazole-4-carboxylate derivative obtained by the process.

SUMMARY OF THE INVENTION

As a result of an intensive investigation in order to solve the above subject matter, the present inventors have found that the desired 5-aminopyrazole-4-carboxylate derivative can be selectively and efficiently formed by directly reacting a hydrazine compound with an alkali metal salt of 2-cyano-3-hydoxy-2-ene-carboxylate which can be simply prepared by a known technique from a readily available carboxylate compound and a cyanoacetate compound. Thus, the present invention has been completed.

That is, one aspect of the invention is a process for preparing a 5-aminopyrazole-4-carboxylate derivative represented by the formula (1):

(1)

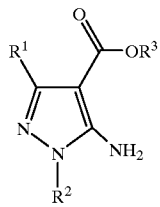

wherein $R^1$ is a straight or branched C1 to C4 alkyl group which can be substituted with a halogen atom, $R^2$ is a hydrogen atom, a straight or branched C1 to C4 alkyl group or an unsubstituted or substituted phenyl group, and $R^3$ is a straight or branched C1 to C4 alkyl group;

comprising reacting a compound represented by the formula (2):

(2)

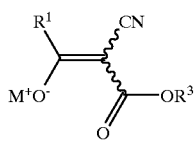

wherein $R^1$ and $R^3$ are the same as above, M is an alkali metal, and kinked line is a single bond showing that the compound of the formula (2) is unrestricted to one of E-isomer or Z-isomer; with a hydrazine compound represented by the formula (3):

(3)

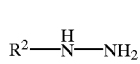

wherein $R^2$ is the same as above, or a hydrate, hydrochloride, hydrobromide or sulfate of the same.

Another aspect of the invention is a 5-aminopyrazole-4-carboxylate derivative represented by the formula (4):

(4)

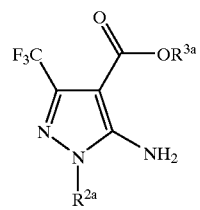

wherein $R^{2a}$ is a straight or branched C1 to C4 alkyl group, and $R^{3a}$ is a hydrogen atom or a straight or branched C1 to C4 alkyl group.

The present invention is quite unique in view of utilizing the alkali metal salt of the compound represented by the formula (2) for the preparation of heterocyclic compound.

DETAILED DESCRIPTION OF THE PREFERRED EMBODIMENTS

In the invention, the desired compound represented by the formula (1) can be prepared according to the reaction formula (C) by reacting the compound represented by the formula (2) with a hydrazine derivative of the formula (3) or hydrate or salt of the same, when necessary, in a solvent.

Reaction Formula (C)

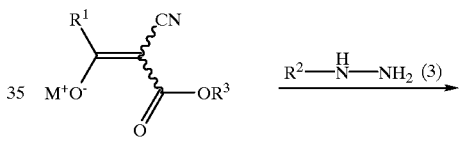

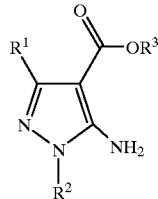

The compound represented by the formula (2) is shown as alkali metal salt in the form of an enol tautomer. Two species of isomers, that is, E-isomer and Z-isomer are present in the alkali metal salt. At the same time, tautomers can exist due to keto-enol equilibrium and thus existence of alkali metal salt of keto tautomer can also be admitted as shown in the reaction formula (D):

Reaction Formula (D)

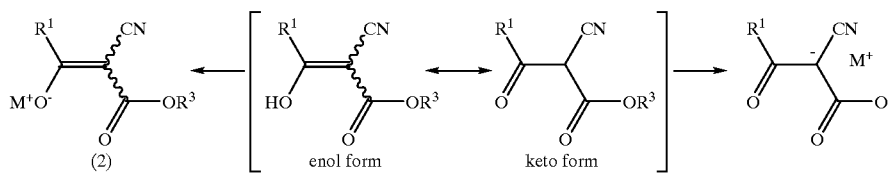

wherein M is an alkali metal atom. In the invention, any of these three isomers can be used for the reaction and the mixture of these isomers can also be used.

In the formula (2), M is an alkali metal atom, preferably sodium atom.

Groups shown by $R^1$ in the formula (1) are unsubstituted or halogen substituted, straight or branched C1 to C4 alkyl groups. Representative groups include, for example, a methyl, ethyl, n-propyl, isopropyl, n-butyl, isobutyl, t-butyl, chloromethyl, dichloromethyl, trichloromethyl, pentachloroethyl, heptachloropropyl, bromomethyl, dibromomethyl, tribromomethyl, fluoromethyl, difluoromethyl, trifluoromethyl and pentafluoroethyl group. Existence of the group can be considered to contribute to the stabilization of the compound represented by the formula (2). In view of high stability, the group is preferably a fluorine substituted straight or branched C1 to C4 alkyl group, more preferably a trifluoromethyl group.

Groups shown by $R^2$ include, for example, a hydrogen atom, a methyl, ethyl, n-propyl, isopropyl, n-butyl, isobutyl, t-butyl group and other straight or branched C1 to C4 alkyl groups; and an unsubstituted or substituted phenyl group. Preferred groups are methyl, ethyl, n-propyl, isopropyl, n-butyl, isobutyl, t-butyl group and other straight or branched C1 to C4 alkyl groups.

Groups shown by $R^3$ include, for example, a methyl, ethyl, n-propyl, isopropyl, n-butyl, isobutyl, t-butyl group and other straight or branched C1 to C4 alkyl groups.

Salts of hydrazine derivatives to be used are preferably monohydrochloride, dihydrochloride, hydrobromide, sulfate and oxalate, more preferably sulfate.

The reaction can be carried out, when necessary, in an inert solvent or diluent. Representative solvents include methanol, ethanol, isopropyl alcohol and other alcohols; diethyl ether, diisopropyl ether, dimethoxyethane, diethoxymethane, 2-methoxyethylether, dioxane, tetrahydrofuran and other ethers; methyl acetate, ethyl acetate, isopropyl acetate, butyl acetate, ethyl propionate and other esters; benzene, toluene, xylene and other aromatic hydrocarbons; dimethyl carbonate, diethyl carbonate, diphenyl carbonate and other carbonate esters; dichloromethane, chloroform, carbontetrachloride, 1,2-dichloroethane, chlorobenzene and other halogenated hydrocarbons; and N,N-dimethylformamide, dimethylsulfoxide, 1-methyl-2-pyrrolidinone and other polar solvents. These solvents can be also used as a mixture.

In the process of the invention, the compound simply represented by the formula (2) can be reacted in the absence of acid with hydrazine compounds represented by the formula (3), or hydrate, hydrochloride, hydrobromide or sulfate of the same. However, the reaction is preferably carried out in the presence of an acid. Acids which can be preferably used include, for example, hydrochloric, sulfuric, phosphoric, boric acid and other mineral acids; formic, acetic, propionic, trifluoroacetic pentafluoropropionic acid and other organic acids; methanesulfonic acid and other organic sulfonic acids; phosphorous pentoxide, sulfur dioxide gas and other acidic oxides; sodium hydrogen sulfate, potassium hydrogen sulfate and other hydrogen sulfate salts; zinc chloride and other Lewis acids; zeolite and other solid acids; and ion exchange resins. Particularly preferred acids are trifluoroacetic acid, pentafluoropropionic acid and other fluorinated carboxylic acids.

Anhydrous magnesium sulfate, anhydrous sodium sulfate, molecular sieves, zeolite and other materials having dehydrating function can also be added to the reaction system.

Other materials which can be also added include a phase transfer catalyst such as tetrabutylammonium chloride, tetrabutylammonium bromide, tetrabutylammonium iodide, benzyltriethylammonium chloride and other quaternary ammonium salts; and crown-ethers such as 12-crown-4,15-crown-5 and 18-crown-6.

The starting materials applied to the reaction of the invention are used in a stoichiometric amount. One of these materials can also be used in excess.

The reaction can be carried out in the temperature range of 0 to 180° C., preferably 20 to 150° C., more preferably at the boiling point of the solvent under the atmospheric pressure or inherent vapor pressure of the solvent.

The reaction time is from 5 minutes to 72 hours, preferably from 3 to 48 hours.

The compound of the formula (2) which is a starting material in the process of the invention can be simply prepared with ease by known techniques from a readily available carboxylate compound and cyanoacetate compound. Marketed hydrazine compounds of the formula (3) can be used for the invention.

The 5-aminopyrazole-4-carboxylate derivative which is obtained by the process of the invention and represented by the formula (1) can be readily converted to a 5-aminopyrazole-4-carboxylic acid derivative by hydrolyzing in the presence of a base such as sodium hydroxide.

In the compounds which can be prepared by the process of the invention and represented by the formula (1), the compound represented by the formula (4), that is, the 5-aminopyrazole-4-carboxylic acid derivative having a trifluoromethyl group on the position 3 of the pyrazole group is a novel compound. Enormous species of compounds including the compound represented by the formula (4) in the invention have been disclosed with a general formula in Japanese Patent Kohyo Publication Hei 6-503069. However, specific description cannot be found on the compound represented by the formula (4) in the invention. The reason is supposed that it is difficult to prepare a compound wherein $R^5$ is a trifluoromethyl group and L is an alkoxy group in the formula (5), that is, the raw material of the formula (1). In fact, the specific description can be found on the raw material.

EXAMPLE

The present invention will hereinafter illustrated in detail by way of examples and reference examples. However, these examples are not construed to limit the scope of the invention.

Reference Example 1

Synthesis of ethyl 2-cyano-3-hydroxy-4,4,4-trifluoro-2-butenoate sodium salt

To a solution obtained by dissolving 24.0 g (1.04 mol) of sodium metal in 400 ml of ethanol, 113.1 g (1.00 mol) of ethyl cyanoacetate was dropwise added with stirring at the room temperature. After stirring for one hour, 150.0 g (1.05 mol) of ethyl trifluoroacetate was dropwise added to the reaction mixture and stirred for 3 hours at the same temperature. After finishing the reaction, the reaction mass was concentrated as intact under reduced pressure. Precipitated solid was the desired product. Ethyl 2-cyano-3-hydroxy-4, 4,4-trifluoro-2-butenoate sodium salt thus obtained was 221.86 g. The yield was 96 %. Following results were obtained by NMR analysis. $^1$H-NMR (acetone-$d_6$, bppm): 1.21(3H, t, J=6.9 Hz), 4.09(2H, q, J=6.9 Hz)

Example 1

Synthesis of ethyl 5-amino-1-methyl-3-trifluoromethylpyrazole-4-carboxylate After suspending 2.31 g (10 mmol) of ethyl 2-cyano-3-hydroxy-4,4,4-trifluoro-2-butenoate sodium salt which was obtained in Reference Example 1 and 2.88 g (20 mmol) of methyl hydrazine sulfate in 20 ml of dimethyl carbonate, the resulting suspension was stirred at 80° C. for 20 hours. The reaction mixture was cooled to room temperature and filtered. The filtrate obtained was concentrated under reduced pressure. The precipitated solid was recrystallized from diisopropyl ether. 0.95 g of desired ethyl 5-amino-1-methyl-3-trifluoromethylpyrazole-4-carboxylate was obtained as white solid. The yield was 40%. No contamination of isomers in the compound was confirmed by gas chromatography. Following results were obtained by NMR analysis.

$^1$H-NMR (CDCl$_3$, δ ppm): 1.34(3H, t, J=7.3 Hz), 3.67 (3H, s), 4.30(2H, q, J=7.3 Hz), 5.24(2H,br)

Melting point: 120–121° C.

Example 2
Synthesis of ethyl 5-amino-1-methyl-3-trifluoromethylpyrazole-4-carboxylate In 20 ml of dimethyl carbonate, 2.31 g (10 mmol) of ethyl 2-cyano-3-hydroxy-4,4,4-trifluoro-2-butenoate sodium salt obtained in Reference Example 1, 2.88 g (20 mmol) of methylhydrazine sulfate and 3.0 g of molecular sieves 3A were suspended and stirred at room temperature. After adding 1.14 g of trifluoroacetic acid, the mixture was stirred for 20 hours at 80° C. The reaction mass was cooled to room temperature and filtered. The resulting filtrate was concentrated under reduced pressure. The separated solid was recrystallized from diisopropyl ether. 2.02 g of the desired ethyl 5-amino-1-methyl-3-trifluoromethylpyrazole-4-carboxylate was obtained as white solid. The yield was 85%. No contamination of isomers in the compound was confirmed by gas chromatography. Following results were obtained by NMR analysis.

$^1$H-NMR (CDCl$_3$, δ ppm): 1.34(3H, t, J=7.3 Hz), 3.67 (3H, s), 4.30(2H, q, J=7.3 Hz), 5.24(2H,br)

Melting point: 120–121° C.

Example 3
Synthesis of methyl 5-amino-1-methyl-3-trifluoromethylpyrazole-4-carboxylate Methyl 2-cyano-3-hydroxy-4,4,4-trifluoro-2-butenoate sodium salt was prepared by similar procedures as Reference Example 1 and reacted by the same procedures as Example 2 to obtain the desired product methyl 5-amino-1-methyl-3-trifluoromethylpyrazole-4-carboxylate as white solid. The yield was 82%. Following results were obtained by NMR analysis.

$^1$H-NMR (CDCl$_3$, δ ppm): 3.66(3H, s), 3.82(3H, s), 5.92(2H,br)

Melting point: 164–165° C.

Example 4
Synthesis of isopropyl 5-amino-1-methyl-3-trifluoromethylpyrazole-4-carboxylate Isopropyl 2-cyano-3-hydroxy-4,4,4-trifluoro-2-butenoate sodium salt was prepared by similar procedures as Reference Example 1 and reacted by the same procedures as Example 2 to obtain the desired product isopropyl 5-amino-1-methyl-3-trifluoromethylpyrazole-4-carboxylate as white solid. The yield was 75%. Following results were obtained by NMR analysis.

$^1$H-NMR (CDCl$_3$, δ ppm): 1.31(6H, d, J=7.2), 3.66(3H, s), 5.09–5.21(3H,m)

Melting point: 108–110° C.

Example 5
Synthesis of 5-amino-1-methyl-3-trifluoromethylpyrazole-4-carboxylic acid To 10 ml of water, 2.37 g (10 mmol) of ethyl 5-amino-1-methyl-3-trifluoromethylpyrazole-4-carboxylate and 0.44 g (11 mmol) of sodium hydroxide were added and stirred at 60° C. for 10 hours. After cooling to room temperature, the reaction mixture was washed with toluene. The resulting aqueous solution was made pH 1 by adding concentrated hydrochloric acid. Precipitate was filtered and dried to obtain 1.78 g of desired 5-amino-1-methyl-3-trifluoromethylpyrazole-4-carboxylic acid as white solid. The yield was 85% Following results were obtained by NMR analysis.

$^1$H-NMR (DMSO-d$_6$, δ ppm): 3.61(3H, s), 6.55(2H,br), 12.40(1H,br)

Melting point: 216–218° C.

Comparative Example 1
Synthesis of ethyl 2-cyano-3-hydroxy-4,4,5,5,5-pentafluoro-2-pentenoate To 20 ml of tetrahydrofuran, 3.39 g (30 mmol) of ethyl cyanoacetate and 6.06 g (60 mmol) of triethylamine were dissolved and stirred at room temperature. Successively, 5.47 g (30 mmol) of pentafluoropropionyl chloride was dropwise added and stirred for 5 hours at room temperature. However, formation of desired product could not be confirmed.

Comparative Example 2
Synthesis of ethyl 5-amino-1-methyl-3-trifluoromethylpyrazole-4-carboxylate To 9 ml of ethanol, 3.0 g (13.2 mmol) of ethyl 3-chloro-2-cyano-4,4,4-trifluoro-2-butenoate was added with stirring and warmed to 72° C. Separately, 0.61 g (13.2 mmol) of methylhydrazine and 1.34 g (13.2 mmol) of triethylamine were dissolved in 6 ml of ethanol and dropwise added to the above solution over 25 minutes. After 2.5 hours, the reaction mass was cooled to room temperature and analyzed by HPLC. Formation of desired product ethyl 5-amino-1-methyl-3-trifluoromethylpyrazole-4-carboxylate was confirmed with the reaction yield of 47%. At the same time, isomers, that is, 4-cyano-5-hydroxy-1-methyl-3-trifluoromethylpyrazole and 4-cyano-3-hydroxy-1-methyl-5-trifluoromethylpyrazole were found with the reaction yield of 42% and 5%, respectively. Isolation of these isomers with a simple method was difficult.

Reaction Formula (E)

Effect of the Invention

The present invention is a novel process for preparing a 5-aminopyrazole-4-carboxylate derivative represented by the formula (1). The process of the invention generally uses raw materials which are readily available and easy to handle, and can eliminate isomer formation which is a problem of conventional preparation process in industry. Even though the isomer is present, the process of the invention is characterized by a simple separation procedure and can reduce preparation step.

Further, the novel 5-amino-3-trifluoromethylpyrazole-4-carboxylate derivative represented by the formula (4) is an important intermediate of medicines and agricultural chemicals, fungicide in particular.

What is claimed is:

1. A process for preparing a 5-aminopyrazole-4-carboxylate derivative represented by the formula (1):

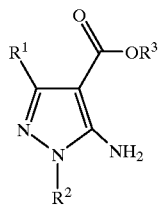

(1)

wherein $R^1$ is a straight or branched C1 to C4 alkyl group which can be substituted with a halogen atom, $R^2$ is a hydrogen atom, straight or branched C1 to C4 alkyl group or an unsubstituted or substituted phenyl group, and $R^3$ is a straight or branched C1 to C4 alkyl group, comprising reacting a compound represented by the formula (2)

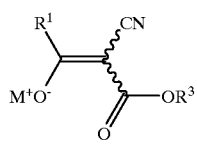

(2)

wherein $R^1$ and $R^3$ are the same as above, M is an alkali metal, and kinked line is a single bond showing that the compound of the formula (2) is unrestricted to one of E-isomer or Z-isomer, with a hydrazine compound represented by the formula (3):

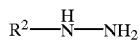

(3)

wherein $R^2$ is the same as above, or a hydrate, hydrochloride, hydrobromide or sulfate of the same.

2. The process for preparing a 5-aminopyrazole-4-carboxylate derivative according to claim 1, wherein the reaction progresses in the presence of an acid.

3. The process for preparing a 5-aminopyrazole-4-carboxylate derivative according to claim 1, wherein the reaction progresses in the presence of dehydrating agent.

4. The process for preparing a 5-aminopyrazole-4-carboxylate derivative according to claim 2, wherein the reaction progresses in the presence of dehydrating agent.

5. The process for preparing a 5-aminopyrazole-4-carboxylate derivative according to claim 1, wherein $R^1$ is a fluorine-substituted, straight or branched C1 to C4 alkyl group.

6. The process for preparing a 5-aminopyrazole-4-carboxylate derivative according to claim 1, wherein $R^1$ is a fluorine-substituted, straight or branched C1 to C4 alkyl group, $R^2$ and $R^3$ are a straight or branched C1 to C4 alkyl group and M is sodium atom.

7. The process for preparing a 5-aminopyrazole-4-carboxylate derivative according to claim 2, wherein $R^1$ is a fluorine-substituted, straight or branched C1 to C4 alkyl group, $R^2$ and $R^3$ are a straight or branched C1 to C4 alkyl group and M is sodium atom.

8. The process for preparing a 5-aminopyrazole-4-carboxylate derivative according to claim 3, wherein $R^1$ is a fluorine-substituted, straight or branched C1 to C4 alkyl group $R^2$ and $R^3$ are a straight or branched C1 to C4 alkyl group and M is sodium atom.

9. The process for preparing a 5-aminopyrazole-4-carboxylate derivative according to claim 4, wherein $R^1$ is a fluorine-substituted, straight or branched C1 to C4 alkyl group.

10. The process for preparing a 5-aminopyrazole-4-carboxylate derivative according to claim 5, wherein the fluorine-substituted, straight or branched C1 to C4 alkyl group is a trifluoromethyl group.

11. The process for preparing a 5-aminopyrazole-4-carboxylate derivative according to claim 1, wherein $R^1$ is trifluoromethyl group and $R^2$ and $R^3$ are a straight or branched C1 to C4 alkyl group.

12. The process for preparing a 5-aminopyrazole-4-carboxylate derivative according to claim 2, wherein $R^1$ is trifluoromethyl group and $R^2$ and $R^3$ are a straight or branched C1 to C4 alkyl group.

13. The process for preparing a 5-aminopyrazole-4-carboxylate derivative according to claim 3, wherein $R^1$ is trifluoromethyl group and $R^2$ and $R^3$ are a straight or branched C1 to C4 alkyl group.

14. The process for preparing a 5-aminopyrazole-4-carboxylate derivative according to claim 4, wherein $R^1$ is trifluoromethyl group and $R^2$ and $R^3$ are a straight or branched C1 to C4 alkyl group.

15. The process for preparing a 5-aminopyrazole-4-carboxylate derivative according to claim 11, wherein M is a sodium atom.

16. The process for preparing a 5-aminopyrazole-4-carboxylate derivative according to claim 12, wherein M is a sodium atom.

17. The process for preparing a 5-aminopyrazole-4-carboxylate derivative according to claim 13, wherein M is a sodium atom.

18. The process for preparing a 5-aminopyrazole-4-carboxylate derivative according to claim 14, wherein M is a sodium atom.

19. A 5-aminopyrazole-4-carboxylate derivative represented by the formula (4):

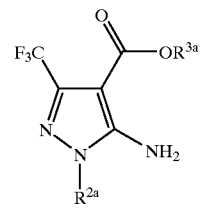

(4)

wherein $R^{2a}$ is a straight or branched C1 to C4 alkyl group, and $R^{3a}$ is a hydrogen atom or a straight or branched C1 to C4 alkyl group.

* * * * *